United States Patent [19]

Herman et al.

[11] Patent Number: 5,462,539

[45] Date of Patent: Oct. 31, 1995

[54] HYGIENE (INCONTINENCE) PAD FOR CATHETER USERS

[76] Inventors: Ella H. Herman, 2325 SW. 17th Cir., Delray Beach, Fla. 33445; Frank Nelams, 234 SW. 12th Ave., Delray Beach, Fla. 33444; Joseph M. Hilbish, 22 Skyline Dr., Upper Saddle River, N.J. 07458

[21] Appl. No.: 268,328

[22] Filed: Jun. 30, 1994

[51] Int. Cl.⁶ .................................................. A61F 13/15
[52] U.S. Cl. ...................... 604/385.1; 604/180; 604/348
[58] Field of Search .................................... 604/305, 307, 604/308, 348, 385.1, 174, 179, 180, 378

[56] References Cited

U.S. PATENT DOCUMENTS

| | | | |
|---|---|---|---|
| 3,161,198 | 12/1964 | Moxley . | |
| 3,895,629 | 7/1975 | Snyder | 604/179 |
| 4,533,968 | 8/1985 | Yoshida et al. . | |
| 4,585,448 | 4/1986 | Enloe | 604/378 |
| 4,588,397 | 5/1986 | Giacalone . | |
| 4,627,846 | 12/1986 | Ternström | 604/385.1 |
| 4,675,015 | 6/1987 | Brown | 604/385.1 |
| 5,009,649 | 4/1991 | Goulter et al. . | |
| 5,263,949 | 11/1993 | Karami et al. . | |

Primary Examiner—Randall L. Green
Assistant Examiner—Rob Clarke
Attorney, Agent, or Firm—Malin, Haley, DiMaggio & Crosby

[57] ABSTRACT

A protective incontinence hygiene pad of laminate construction for catheter patients who have urinary and bowel incontinence. The pad includes at least one peripheral notched area that permits a catheter tube to pass therethrough with sealable areas around the notch so that the device can be sealed to prevent the escape of both liquid and solid materials from the pad while it is being worn by the user. The notch has an adhesive tab or tape proximate its peripheral edges that secures the catheter within the notch, which helps stabilize the catheter in position while retaining the seal around the pad between the skin of the wearer and the pad.

14 Claims, 1 Drawing Sheet

HYGIENE (INCONTINENCE) PAD FOR CATHETER USERS

BACKGROUND OF THE INVENTION

1. Field of the Invention

A protective incontinence hygiene pad for urethral catheter patients and in particular, a hygiene pad of increased comfort that is disposable for incontinent patients, such as stroke victims that also require a urethral catheter line, particularly with male patients.

2. Description of the Prior Art

The use of disposable diaper or diaper-like barriers for use with incontinent persons is well known in the prior art. U.S. Pat. No. 5,263,949, issued Nov. 23, 1993 to Karami et al., shows a disposable diaper with a barrier sheet that prevents waste material from escaping through the back of the diaper or through the sides of the pad. U.S. Pat. No. 5,009,649, issued Apr. 23, 1991 to Goulter et al., shows a male undergarment for urinary incontinence.

Certain incontinence patients, such as stroke victims, who are either ambulatory or bedridden, require urinary catheters that are either inserted in the penis for males or the vagina for females for urinary incontinence, while at the same time requiring a conventional pad for bowel material incontinence. Drawbacks of the present pads used for incontinence are that they are bulky to the point of extreme discomfort, especially in the crotch area, and that there is no provision to accommodate a peripheral urethral catheter that must pass around or through the pad areas, while creating a seal that insures total sealing of the pad around the lower area of the body of the user to treat total incontinence.

The present invention provides for a very comfortable sealed pad that fits around the lower abdomen and genital area of the wearer that can prevent waste materials from leaking or falling from the pad, while at the same time accommodating a urethral catheter tube that can extend from the male or female organ and pass around the perimeter of the pad while the pad remains sealed. The reduction of bulkiness in the crotch area prevents chaffing and soreness, and is more comfortable for the wearer in any position.

SUMMARY OF THE INVENTION

A protective incontinence hygiene pad of laminate construction for urethral catheter patients who have urinary and bowel incontinence. The pad includes a substantially rectangularly shaped plastic barrier layer base having recessed side indentations for a narrow crotch portion which accommodate the interior leg portions of the user. The size of the overall pad extends around the torso, front, and rear of the wearer, and includes a waist attachment for the wearer. The perimeter of the base layer has a plastic overlap and elastic portion which include a sealing portion that can expand and contract, especially around the crotch area, which allows for conformity to the leg of the person on each side and a tight seal to be formed around the body portions of the wearer. The pad includes at least one, and preferably two, peripheral notched areas (one on the left, the other on the right) that permit a urethral catheter to pass therethrough with sealable areas around the notch so that the device can be sealed to prevent the escape of both liquid or solid materials from the pad while it is being worn by the user. The pad can also be worn by non-catheter users with low urinary leakage (e.g. "dribblers") to ensure added social comfort.

The outer layer of the pad has a waterproof plastic thin barrier sheet that is plastic and prevents moisture, liquid, or semi-liquid materials from passing therethrough, permitting a plastic exterior wide edge to surround the entire outside periphery of the padded layer. The inner layer is a liquid pervious thin cover which typically is of substantially the same configuration and dimensions as the base layer, wherein the respective layers are secured together around their common periphery.

Predetermined areas between the inner layer and the outer layer contain absorbent padding of standard absorbent materials and are of sufficient thickness to prevent waste matter from passing or falling therethrough. More specifically, the rear area of the pad is fully padded with absorbent material for solid waste incontinence, while the front area of the pad is padded with a much narrower or thinner padding, in that the bulk is not necessary for catheter wearers since the urine flows from the internal/external tubing into a bag. Consequently, a narrower padding between the legs improves comfort in the front and crotch area. In addition, thinner abdominal padding improves comfort and appearance.

The device includes a waist band, unitarily attached to the ends of the pad, that has sticky portions for temporary attachment to the wearer so that the entire pad is disposable.

To utilize the garment, the recessed side walls are placed between the legs in the crotch area of the wearer and the rear portion and front portions are brought up around the torso and fastened with the waistband. Therefore the garment is firmly attached to the wearer. Prior to final installation of the pad around the wearer, the catheter is positioned from the male or female organ through a notch, the notch having a tab or tape proximate its peripheral edges that secures the catheter within the notch in the side wall of the pad, which helps stabilize the catheter itself (which may be ¼" to ½" in diameter) in position while retaining the seal around the pad between the skin of the wearer and the pad.

The catheter is secured in the wearer's bladder by a small balloon. If the catheter tube receives any stress, the balloon waivers, thereby allowing for leakage down the catheter tube. Any urine spilled through use of the catheter will be absorbed by the pad, while any feces will be firmly sealed within the pad until the pad is changed. This eliminates a non-sealing condition which can be caused by the placing of the catheter through the pad periphery or around the pad periphery.

It is an object of this invention to provide an improved, comfortable hygiene pad for ambulatory or non-ambulatory incontinent patients that require the use of a urinary catheter.

It is another object of this invention to provide a hygiene pad that can be used in conjunction with a urethral catheter that helps to stabilize the catheter in position when in use in conjunction with a hygiene pad used for fecal incontinence.

It is another object of this invention to provide a disposable, easily usable hygiene pad for incontinent patients that require the use of a catheter.

In accordance with these and other objects which will become apparent hereinafter, the instant invention will now be described with particular reference to the accompanying drawings.

DESCRIPTION OF THE PREFERRED EMBODIMENTS

Figure 1:
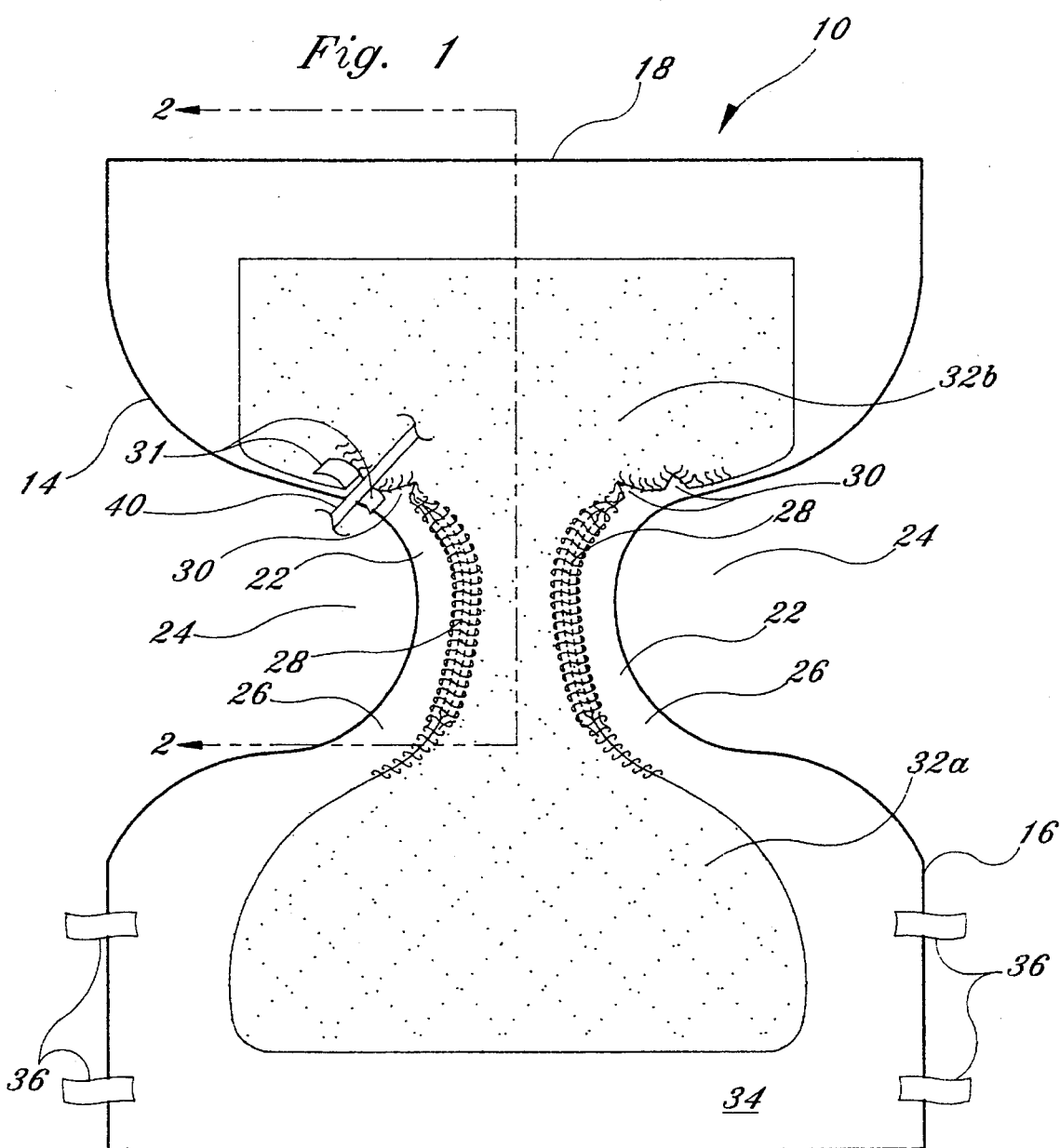
FIG. 1 shows a top plan view of a hygiene pad in accordance with the present invention.
Figure 2:
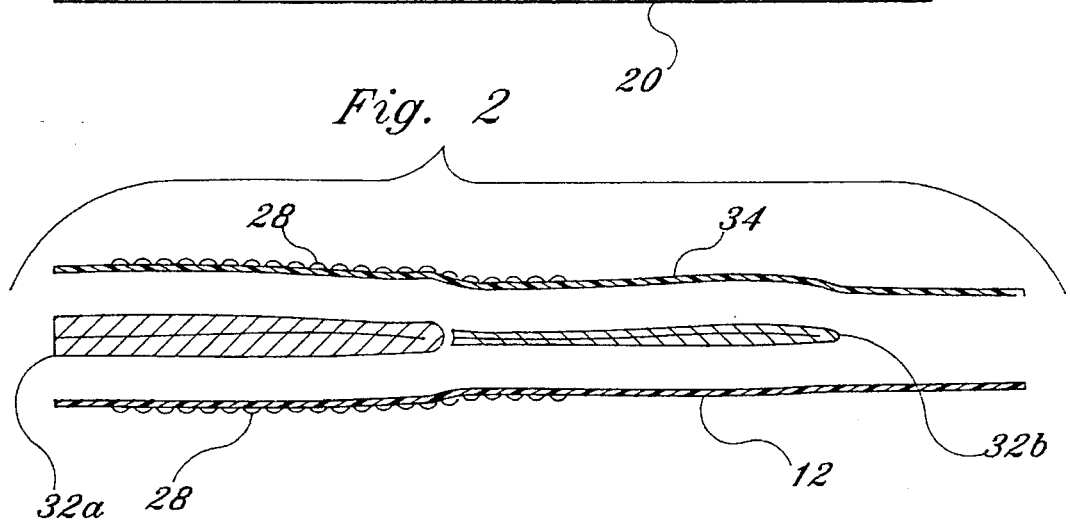
FIG. 2 shows an exploded side cross sectional view of a hygiene pad in elevation in accordance with the present invention.

Referring now to FIGS. 1 and 2, a protective incontinence hygiene pad 10 of the present invention has its periphery defined by a liquid imperious backing or back sheet 12 having opposed side edges 14 and 16, and a pair of opposed end edges 18 and 20 connecting the side edges 14 and 16.

The hygiene pad 10 has a crotch portion 22, i.e., a portion to engage the crotch area of the wearer to capture body waste material. Cutout portions 24 are shown on opposed sides of the crotch portion 22 such that the hygiene pad 10 has a generally hourglass configuration. The perimeter of the base layer has a plastic overlap 26 and elastic portion 28 which can expand and contract, especially around the crotch area 22, which allows for conformity to the leg of the person on each side and a tight seal to be formed around the body portions of the wearer. The pad 10 includes at least one peripheral notched area 30 proximate the crotch area 22 that permits a catheter tube 40 to pass therethrough, with sealable elastic areas around the notch so that the incontinence pad can be sealed to prevent the escape of both liquid and solid materials from the pad while it is being worn by the user. The notch 30 has an adhesive tab or tape 31 proximate its peripheral edges that secures the catheter within the notch in the side wall of the pad, which helps stabilize the catheter in position while retaining the seal around the pad between the skin of the wearer and the pad. The notch area 30 secures the catheter tube 40 traveling from the penis or vagina, thereby eliminating painful twisting and pulling on the tube when the user is walking, standing, sitting, etc.

The hygiene pad 10 has an absorbent pad 32a, 32b seated on an inner surface of the back sheet 12 for capturing and retaining body waste material. Absorbent pad 32a, 32b may be made of any standard absorbent materials and is of sufficient thickness to prevent waste matter from passing or falling therethrough.

An important aspect of the instant invention is shown in FIG. 2, wherein the rear area of the pad is fully padded with absorbent material for solid waste incontinence, while the front area of the pad is padded with significantly less and much narrower padding (e.g. the padding is not as thick between the back sheet 12 and the cover sheet 34), in that the bulk is not necessary for catheter wearers since the urine flows from the internal/external tubing into a bag. Consequently, a narrower padding in the front of the pad between the legs improves comfort in the front and crotch area. This is a significant improvement over prior art devices. Furthermore, as seen in FIG. 1, because the amount of padding is significantly reduced in and around the crotch area, cutout portions 24 are more pronounced than in standard diapers, allowing the distance between their opposing edges to be reduced, thereby allowing for a more conforming and more comfortable fit.

Preferably, a front or cover sheet 34 is also provided. The cover sheet 34, which is liquid pervious, is shown to be of substantially the same configuration and dimensions as the back sheet 12 and the respective sheets are secured together at least around their common periphery. However, it is to be understood that cover sheet 34 may only cover the absorbent pad 32, wherein cover sheet 34 will be sealed around its periphery to the back sheet 12 just beyond the absorbent pad's periphery.

A pair of conventional fasteners 36 in the waist area permit releasable securing or refastening of the opposed end edges 18 and 20 together around the waist when the hygiene pad is folded to engage the front and back of the user's body.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An incontinence pad for catheter users to be worn around the lower abdomen and genital area body portions of a wearer, comprising:

a liquid impervious back sheet defining the shape and dimensions of said incontinence pad;

a crotch portion adapted to engage the crotch of a wearer to capture and retain body waste material when said incontinence pad is folded medially and worn engaging a waist area of the wearer, said crotch portion having elastic along the periphery thereof which allows for conformity to a leg of the wearer on each side and a tight seal to be formed around the leg of the wearer;

an absorbent pad for receiving body waste material connected to an inner surface of said back sheet, said incontinence pad having a front area and a rear area, said absorbent pad being thinner in the front area of said incontinence pad than in the rear area of said incontinence pad, thereby improving wearer comfort; and at least one peripheral notched area proximate the crotch portion for permitting a urethral catheter tube to pass therethrough, said at least one peripheral notched area including means for securing the catheter tube within the at least one peripheral notched area proximate a peripheral edge of said at least one peripheral notched area.

2. An incontinence pad as recited in claim 1, further comprising a liquid pervious cover sheet covering a front surface of said incontinence pad.

3. An incontinence pad as recited in claim 1, including a cutout portion on each opposing side of said crotch portion, whereby said incontinence pad has a substantially hourglass shape.

4. An incontinence pad as recited in claim 1, including waist fasteners for releasably securing said incontinence pad around the waist of the wearer.

5. An incontinence pad as recited in claim 1, wherein said incontinence pad includes an elastic area proximate the notched area so that said incontinence pad is sealed to prevent an escape of body waste material from said incontinence pad while it is being worn by the user.

6. An incontinence pad as recited in claim 1, wherein said means for securing is a tab having an adhesive portion disposed thereon.

7. An incontinence pad as recited in claim 1, wherein said means for securing is tape having an adhesive portion disposed thereon.

8. An incontinence pad for catheter users to be worn around the lower abdomen and genital area body portions of a wearer, comprising:

a liquid impervious back sheet defining the shape and dimensions of said incontinence pad;

a crotch portion adapted to engage the crotch of a wearer to capture and retain body waste material when said incontinence pad is folded medially and worn engaging a waist area of the wearer, said crotch portion having elastic along the periphery thereof which allows for conformity to a leg of the wearer on each side and a tight seal to be formed around the leg of the wearer;

an absorbent pad for receiving body waste material connected to an inner surface of said back sheet, said incontinence pad having a front area and a rear area, said absorbent pad being thinner in the front area of said incontinence pad than in the rear area of said incontinence pad, thereby improving wearer comfort; and at least one peripheral notched area proximate the crotch portion for permitting a urethral catheter tube to pass therethrough, said notched area including a means for securing the catheter tube within the notched area proximate a peripheral edge of said notched area, thereby eliminating painful twisting and pulling on the catheter tube when the user is walking, standing, or sitting.

9. An incontinence pad as recited in claim 8, wherein said incontinence pad includes an elastic area proximate the notched area so that said incontinence pad is sealed to prevent an escape of body waste material from said incontinence pad while it is being worn by the user.

10. An incontinence pad as recited in claim 8, further comprising a liquid pervious cover sheet covering a front surface of said incontinence pad.

11. An incontinence pad as recited in claim 8, including a cutout portion on each opposing side of said crotch portion, whereby said incontinence pad has a substantially hourglass shape.

12. An incontinence pad as recited in claim 8, including waist fasteners for releasably securing said incontinence pad around the waist of the wearer.

13. An incontinence pad as recited in claim 8, wherein said means for securing is a tab having an adhesive portion disposed thereon.

14. An incontinence pad as recited in claim 8, wherein said means for securing is tape having an adhesive portion disposed thereon.

\* \* \* \* \*